US012642577B2

(12) United States Patent
Rousseau

(10) Patent No.: US 12,642,577 B2
(45) Date of Patent: Jun. 2, 2026

(54) ELECTROSURGICAL FORCEPS COMPRISING A SUCTION DEVICE

(71) Applicant: Magnitude Surgical, Omet (FR)

(72) Inventor: Nicolas Rousseau, Omet (FR)

(73) Assignee: Magnitude Surgical, Omet (FR)

( * ) Notice: Subject to any disclaimer, the term of this patent is extended or adjusted under 35 U.S.C. 154(b) by 790 days.

(21) Appl. No.: 18/004,608

(22) PCT Filed: May 28, 2021

(86) PCT No.: PCT/FR2021/050972
§ 371 (c)(1),
(2) Date: Jan. 6, 2023

(87) PCT Pub. No.: WO2022/008808
PCT Pub. Date: Jan. 13, 2022

(65) Prior Publication Data
US 2023/0240743 A1 Aug. 3, 2023

(30) Foreign Application Priority Data
Jul. 8, 2020 (FR) ...................................... 2007202

(51) Int. Cl.
*A61B 18/14* (2006.01)

(52) U.S. Cl.
CPC .. *A61B 18/1442* (2013.01); *A61B 2018/1455* (2013.01)

(58) Field of Classification Search
CPC ...... A61B 18/1442; A61B 2018/00202; A61B
2018/00595; A61B 2018/00601; A61B
2018/1405; A61B 2018/1412; A61B
2018/1455; A61B 2218/002; A61B
2218/008
See application file for complete search history.

(56) References Cited

U.S. PATENT DOCUMENTS

| | | | |
|---|---|---|---|
| 6,926,717 B1 | 8/2005 | Garito et al. | |
| 2003/0139743 A1 | 7/2003 | Spitzer | |

(Continued)

FOREIGN PATENT DOCUMENTS

| | | |
|---|---|---|
| EP | 2153791 B1 | 5/2014 |
| WO | 2015/193627 A1 | 12/2015 |

OTHER PUBLICATIONS

International Search Report for International Application No. PCT/FR2021/050972 dated Sep. 1, 2021, 2 pages.

(Continued)

*Primary Examiner* — Khadijeh A Vahdat
(74) *Attorney, Agent, or Firm* — TraskBritt

(57) ABSTRACT

An electrosurgical forceps comprises a first arm and a second arm connected by a pivot joint for moving the arms toward and away from one another. The two arms have a distal end and a proximal end. A first electrode and a second electrode are disposed at the distal ends of the first arm and the second arm, respectively. The electrosurgical forceps comprise a channel extending in the first arm to terminate at the distal end thereof in a suction conduit having a main opening and an axial opening. The second arm is configured to at least partially close the main opening of the suction conduit when the two arms are in a position moved toward one another.

18 Claims, 3 Drawing Sheets

(56)              References Cited

U.S. PATENT DOCUMENTS

| | | |
|---|---|---|
| 2007/0255272 A1 | 11/2007 | Ariola |
| 2010/0087814 A1 | 4/2010 | Desinger et al. |
| 2011/0306967 A1 | 12/2011 | Payne et al. |
| 2013/0066317 A1* | 3/2013 | Evans .................. A61B 18/042 |
| | | 606/48 |
| 2017/0281262 A1* | 10/2017 | Rousseau ........... A61B 18/1442 |
| 2017/0319264 A1 | 11/2017 | Haupt |

OTHER PUBLICATIONS

International Written Opinion for International Application No. PCT/FR2021/050972 dated Sep. 1, 2021, 6 pages.

* cited by examiner

ELECTROSURGICAL FORCEPS COMPRISING A SUCTION DEVICE

CROSS-REFERENCE TO RELATED APPLICATIONS

This application is a national phase entry under 35 U.S.C. § 371 of International Patent Application PCT/FR2021/050972, filed May 28, 2021, designating the United States of America and published as International Patent Publication WO 2022/008808 A1 on Jan. 13, 2022, which claims the benefit under Article 8 of the Patent Cooperation Treaty to French Patent Application Serial No. FR2007202, filed Jul. 8, 2020.

TECHNICAL FIELD

The present disclosure relates to an electrosurgical forceps comprising a suction device for extracting the smoke likely to be emitted during a procedure. The present disclosure applies more particularly to a bipolar surgical forceps comprising two electrodes disposed at the respective ends of two articulated arms.

BACKGROUND

Monopolar and bipolar electrosurgical devices are widely used in surgical settings to incise, manipulate and/or cauterize tissue. However, the smoke emitted by these instruments during their use is likely to contain chemical elements that, if inhaled, may be harmful for both the patient's and the surgeon's health. This smoke may contain, in particular, irritating and/or carcinogenic substances. It is therefore desirable to limit the risk of contamination by having surgical forceps capable of sucking up the generated smoke to prevent it from being inhaled.

Such a forceps is known from document US20170319264. The proximal end of this forceps is connected to a suction device and the internal walls of the forceps arms are configured to form, in combination, a suction duct when these two arms are pressed against each other to cauterize tissue.

Document WO2015193627 discloses a general-purpose electrosurgical forceps that can be used for gripping, incision and cauterization. This forceps can treat tissues in these different operating modes without necessarily adjusting the energy level and/or the waveform delivered by the generator during the procedure. A first electrode, disposed at the distal end of a first arm, has a concave cross-section, capable of at least partially housing a second electrode. The second electrode, which is disposed at the distal end of a second arm articulated to the first arm, projects from the first electrode when the two arms are brought toward one another. As specified in detail in the aforementioned document, the forceps can be used according to several different modes of operation. In each of these modes, a particular portion of the electrodes is placed in contact with the tissues. Consequently, the precise origin of the smoke generated during the use of this forceps varies according to the mode of operation used.

It would be desirable to be able to have an electrosurgical forceps provided with a suction device allowing efficient suction of the smoke independently of the mode of operation chosen.

BRIEF SUMMARY

An object of the present disclosure is to provide such an electrosurgical forceps comprising a smoke suction device.

Another object of the present disclosure is to provide a smoke suction device that can be fitted to an existing electrosurgical forceps.

In order to achieve this aim, the object of the present disclosure proposes an electrosurgical forceps comprising:

- a first arm and a second arm connected by a pivot joint for moving the arms toward and away from one another, the two arms having a distal end and a proximal end; and
- a first electrode and a second electrode disposed at the distal ends of the first arm and the second arm, respectively.

The electrosurgical forceps further comprise a channel extending in the first arm to terminate at the distal end thereof in a suction conduit having a main opening and an axial opening, and in that the second arm is provided with a shutter element configured to at least partially plug the main opening of the suction conduit when the two arms are in a position moved toward one another.

According to other advantageous and non-limiting features of the present disclosure, taken individually or in any technically feasible combination:

- the suction conduit is formed by two side walls and a base, the base comprising a spout to receive the first electrode and to prevent a suction flow at the base of this first electrode;
- the walls comprise, on their internal surface, guide elements to direct the smoke toward the suction duct;
- the second electrode has the shape of a blade having a flat surface, and the shutter element comprises two flats disposed parallel to the flat surface;
- the second electrode comprises a manipulator for rotating the second electrode on itself;
- the first arm also comprises an irrigation channel opening onto an irrigation nozzle disposed directly under the first electrode;
- the channel is disposed in a longitudinal body assembled to the first arm;
- the longitudinal body is clipped to the first arm using a pair of notches disposed on a proximal part of the longitudinal body;

According to another aspect, the object of the present disclosure proposes a suction device for an electrosurgical forceps comprising a longitudinal body intended to be assembled with a first arm of the forceps, the suction device comprising a channel extending in and along the longitudinal body to terminate, at the side intended to receive the distal end of the forceps, in a suction conduit having a main opening and an axial opening;

Advantageously, the conduit comprises a rear cover provided with a passage for receiving the distal end of the first arm of the forceps.

BRIEF DESCRIPTION OF THE DRAWINGS

Further features and advantages of the present disclosure will become apparent from the following detailed description of example embodiments of the present disclosure, with reference to the appended figures, in which.

DETAILED DESCRIPTION

Figures 1, 2:
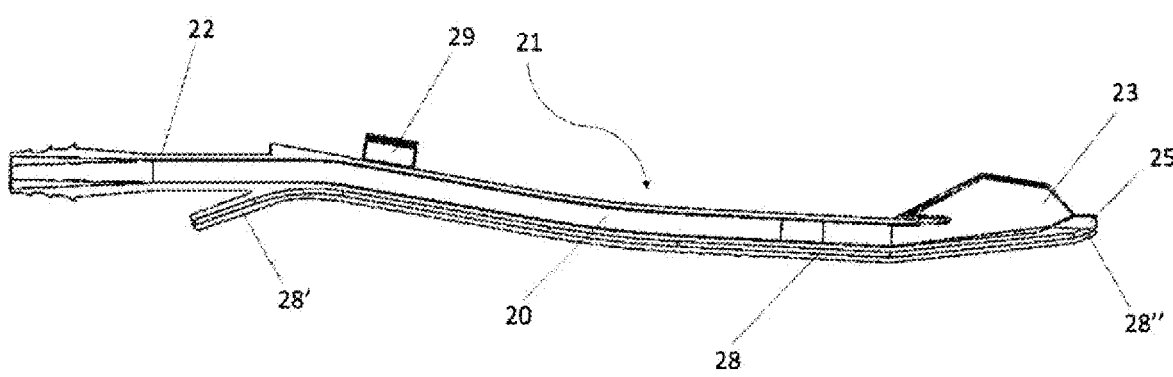
FIG. 1 is a perspective view of an electrosurgical forceps according to the present disclosure.
FIG. 2 is a cross-sectional side view of the longitudinal body of a suction device according to the present disclosure.

Referring to FIG. 1, the forceps 10 comprise a first arm 11 and a second arm 12 that are connected by a pivot joint for bringing the arms 11, 12 toward and away from one another. The pivot joint here is positioned at the proximal end of each arm, but it could just as well be placed in the central part of the arms 11, 12 to form scissors. The forceps 10 are electrically connected to a generator (not shown in the figures) capable of generating high-frequency signals leading to the performance of treatments, such as an incision and/or cauterization. It may be a current generator.

The forceps 10 also comprise a first electrode 13a and a second electrode 13b disposed at the distal ends 11a, 12a of the first arm 11 and the second arm 12, respectively. The electrodes 13a, 13b are in electrical connection with the generator, for example, via a cable integrated into the arms 11, 12 to form a first and second electrical contact with the biological tissues, and to close current lines on these tissues. The first electrode 13a has a concave cross-section, capable of partly housing the second electrode 13b, here in the form of a blade having a flat surface and an edge that can both be used during a treatment. The second electrode 13b projects from the first electrode 13a when the two arms 11, 12 are in a position close to each other.

In the example shown, the electrosurgical forceps are provided with a suction device. This suction device is formed by a longitudinal body 21 assembled to the first arm 11, shown in section in FIG. 2, and a shutter element 26 disposed on the second arm 12.

The longitudinal body 21 has, at a first end, a connector 22 for connecting a channel 20 to a suction duct of an external equipment item. The channel 20 is formed, at its second end opposite the first end, by a suction conduit 23 intended to receive the distal end 11a of the first arm 11. The suction conduit 23 has an upper opening 24a, which will be called the main opening 24a below, and an axial opening 24b (FIG. 4), which are both used to evacuate the smoke, as will be detailed later in this description. When the longitudinal body 21 is suitably assembled to the forceps, at least part of the first electrode 13a projects from the suction conduit 23.

As can be seen in FIG. 2, the channel 20 is a closed channel that is buried over part of its length in the longitudinal body 21. This closed portion of the channel opens on one side to the suction conduit 23 and on the other to the connector 22. The channel 20 makes it possible to evacuate the smoke formed at the distal end of the forceps 10, in the environment close to the electrodes 13a, 13b and captured by at least one of the openings 24a, 24b of the suction conduit 23, toward the suction duct. The conduit 23 therefore forms a suction nozzle for this smoke, and its configuration allows the fumes to be sucked up efficiently in the multiple modes of operation of the forceps.

Figure 3:
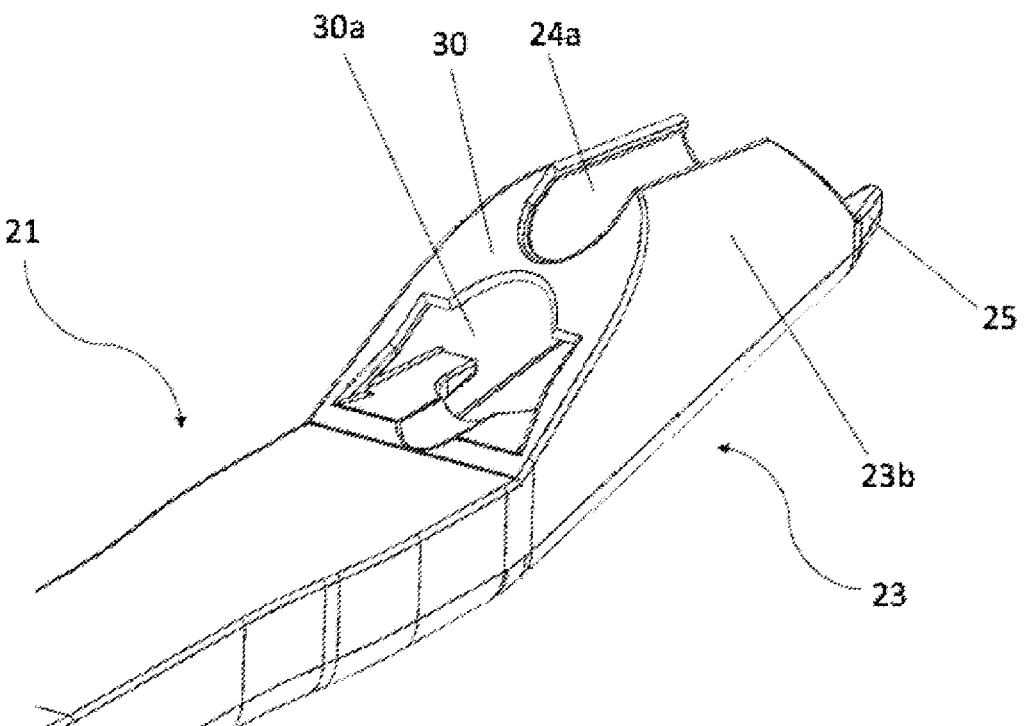
FIG. 3 is a perspective view of a conduit of the suction device of FIG. 2.

FIG. 3 shows a perspective view of the suction conduit 23, on which the main opening 24a of the conduit 23 is clearly visible. A rear cover 30 is provided with a passage 30a conforming to the outline of the distal end 11a of the first arm 11 of the forceps. The forceps 10 is assembled to the longitudinal body 21 by introducing the distal end 11a of the first arm 11, carrying the first electrode 13a, through the passage 30a. In the assembled position, the passage 30a is completely closed off by the first arm 11 of the forceps, which limits or eliminates any parasitic suction flow at this passage 30a when the suction mechanism of the forceps is activated. To securely retain the longitudinal body 21 on the first arm 11, the longitudinal body 21 is provided with a retaining element 29, here a pair of notches 29 disposed on a proximal part, to clip onto the first arm 11.

Figure 4:
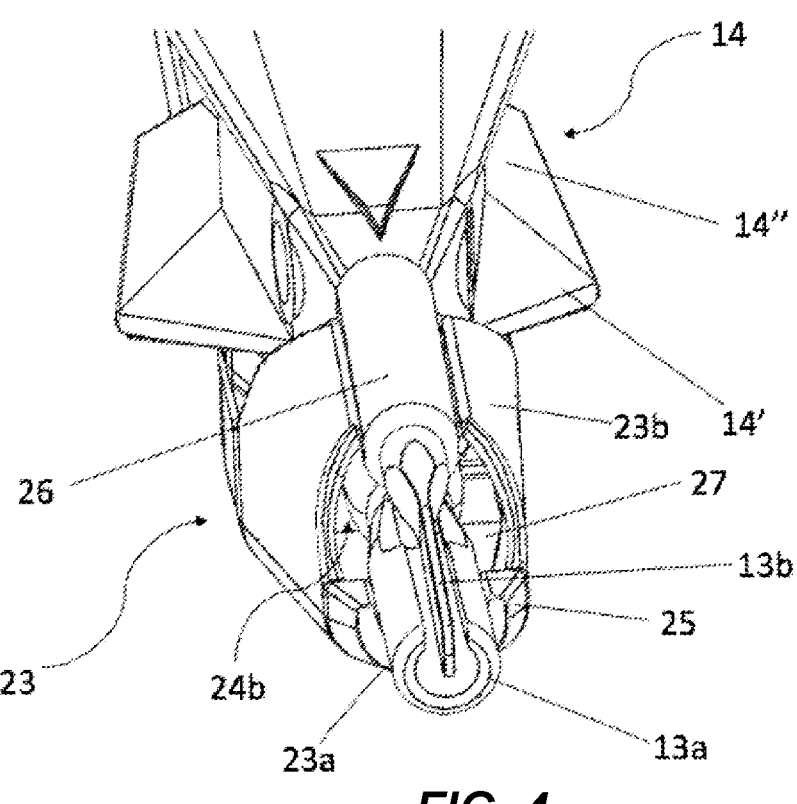
FIGS. 4 and 5 show the distal end of a forceps according to the present disclosure, in two different modes of operation, respectively.
Figure 5:
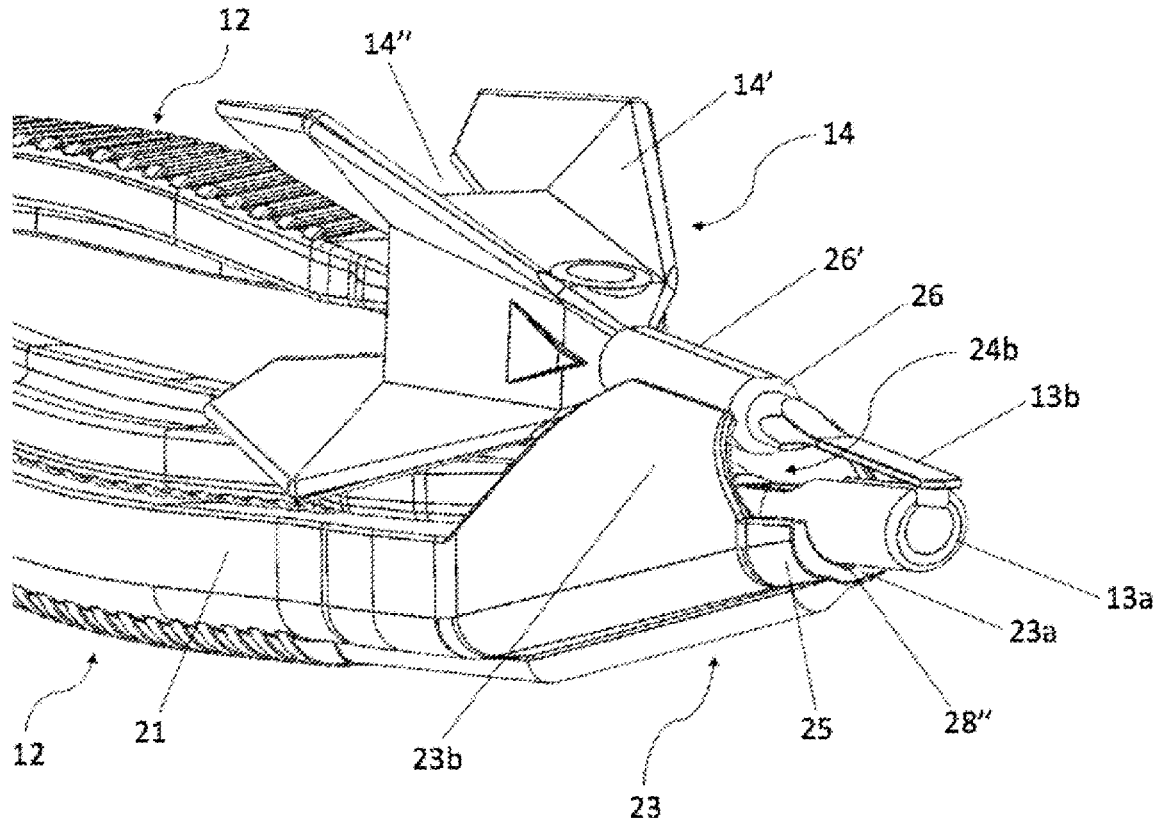

As can be seen in FIGS. 4 and 5, the suction conduit 23 comprises a base 23a ending in a spout 25 having a recess for receiving and carrying the first electrode 13a. The suction conduit 23 also comprises two side walls 23b defining the main and axial openings. The suction channel 20 opens into the base 23a of the conduit 23, as is clearly visible in FIG. 2. The conduit has a dimension such that a lateral spacing exists between the first arm 11, the first electrode 13a and the walls 23b. This spacing, which can be between 1 mm and 5 mm on each side of the first electrode 13a, defines the axial opening 24b allowing suction as close as possible to the first electrode 13a, as is clearly visible in FIG. 4. Similarly, the distance separating the two walls 23b at their free ends defines the main opening 24a of the conduit 23.

The lateral parts of the spout 25, on either side of the recess receiving the first electrode 13a, make it possible to prevent suction that is too close to this electrode 13a. This avoids sucking in fluids or other unwanted elements that could block and/or damage the suction channel 20. As can be seen in FIG. 2, the side parts of the spout 25, inside the conduit 23, are shaped like ramps so as to properly direct the axial suction flow.

Advantageously, the walls 23b may comprise, on their internal surfaces, oriented toward the interior of the suction conduit 23, guide elements 27 to direct the smoke drawn in toward the opening of the suction channel 20.

The second arm 12 of the forceps is configured to at least partially close the main opening 24a of the suction conduit 23 when the two arms 11, 12 are in a position close to one another. For this purpose, the second arm 12 is provided with the shutter element 26. The shutter element 26 is disposed along this arm 12 to be opposite the main opening 24a of the conduit 23 and allow positioning between the two side walls 23b by bringing the two arms 11, 12 closer together. The shutter element 26 here is in the form of a substantially cylindrical part, fitted onto the second arm 12. By closing the suction conduit using the shutter element 26, even partially, the suction flows are reinforced at the axial opening of the conduit and the evacuation of the smoke produced in the direct environment of this opening is improved.

Returning to the description of FIG. 1, the second arm 12 of the forceps is advantageously provided with a manipulator 14 making it possible to move the second electrode 13b in rotation on itself (about an axis coinciding with this electrode) and to position the latter according to different orientations with respect to the first electrode 13a. The manipulator 14 here takes the form of a rosette element 14 having four wings 14' defining four slots 14" making it possible to receive the first arm 11 when the two arms 11, 12 are moved toward one another. The rosette element 14 is free to move in rotation about an axis substantially defined by the longitudinal axis of the second arm 12, and rotates the second electrode 13b and the shutter element 26.

The two electrodes 13a, 13b (when the second arm is brought closer to the first) project from the suction conduit 23 so that this conduit (and more generally, the suction device) does not interfere with the use of the forceps during a procedure. The main opening 24a of the suction conduit 23, in particular, allows the second arm to be freely brought closer to the first, and the second electrode 13b to be positioned close to the first electrode 13a (FIG. 5) or to be housed in the concavity of this first electrode (FIG. 4), allowing unhindered operation of the electrosurgical forceps in all its modes of operation according to the teaching of document WO2015193627.

When the two arms 11, 12 of the forceps are open, in a configuration allowing the gripping of the tissues between the two electrodes 13a, 13b, the main opening 24a of the conduit is not closed by the shutter element 26, and so-called "radial" suction can flow through this opening, as close as possible to the tissues, to evacuate any smoke that may be emitted.

In another mode of operation shown in FIG. 5, the second blade-shaped electrode 13b is oriented and positioned using the rosette element 14 so that its flat surface overhangs the first concave electrode 13a. In this configuration, the shutter element 26 completely obstructs the opening 24a of the conduit 23, and comes as close as possible to the walls 23b of the conduit 23, for example, less than 0.2 mm from these walls. This limits or prevents the presence of a radial flow through the main opening 24a, to favor the axial suction flow, making it possible to suck in the smoke produced at the end of the flat surface of the second electrode 13b, for example, when the latter works in cauterization.

In yet another mode of operation shown in FIG. 4, the second blade-shaped electrode 13b is oriented and positioned using the rosette element 14 to be partially housed in the concavity of the first electrode 13a.

In this configuration, the second arm 12 is disposed closest to the first arm 11, and the shutter element 26 penetrates slightly deeper between the two walls 23b, and engages slightly deeper in the conduit 23. Since the shutter element 26 has a cylindrical shape, this engagement releases play between the shutter element 26 and each of the walls 23b. This play, which can be of the order of a millimeter, makes it possible to develop a radial suction flow making it possible to suck in the smoke produced close to the cutting edge of the second electrode 13b, for example, when the latter works in incision. Of course, the shutter element 26 can have a shape other than the cylindrical shape shown in the figures, any shape varying its transverse dimension according to its degree of engagement in the conduit 23 making it possible to obtain the same effect.

In a particular embodiment, which is optional but very advantageous to promote the development of the radial suction flow in the configuration that has just been described, the cylindrical shutter element 26 can be provided on its external surface with two diametrically opposed flats 26'. The surfaces of these flats 26' are parallel to the flat surface of the second electrode 13b. The flats 26' make it possible to reduce the transverse dimension of the shutter element 26 in this configuration. Thus, when the second electrode 13b is oriented using the rosette element 14 to be able to be housed in the concavity of the first electrode 13a, the flats 26' are oriented to face the walls 23b of the conduit. The shutter element 26 then partially fills the opening 24a of this conduit 23, which promotes the development of the radial suction flow.

In addition to a suction channel 20, the longitudinal body 21 can be provided with an irrigation channel 28, visible in FIG. 2. The irrigation channel 28 is advantageously disposed substantially parallel to the suction channel 20. This irrigation channel 28 is also closed and integrated into the longitudinal body 21. It leads to a secondary connector 28' to be connected to an irrigation duct of an equipment item, configured to dispense a liquid into this channel. On the other side of the longitudinal body 21, the irrigation channel 28 leads to an irrigation nozzle 28". The irrigation nozzle 28" emerges at the spout 25 of the base 23a of the suction conduit 23, directly under the first electrode 13a, that is to say, in contact with this electrode. In this way, the fluid circulating in the irrigation channel 28 can bead and/or trickle along this electrode 13a to reach the tissues, regardless of the orientation of the forceps and the electrodes. In an alternative configuration not shown in the figures, the irrigation nozzle 28" does not open out directly under the first electrode 13a. Provision can be made in this case for the irrigation channel to have, on the side of the first electrode, an elbow allowing the channel to emerge at a distance from the first electrode. By thus moving the irrigation nozzle away from the first electrode, the risk of sucking the liquid that flows from the nozzle into the suction channel is limited.

As will be readily understood, the present disclosure is not limited to the described embodiment, and it is possible to add variants thereto without departing from the scope of the invention as defined by the claims.

The suction device (and, in particular, the longitudinal body) has been presented and described as a separate element that can be assembled with the electrosurgical forceps, which forms an important advantage of the present disclosure. One can naturally consider integrating the suction device monolithically into the forceps, and, in particular, integrating the longitudinal body into the first arm of the forceps. Generally therefore, whether or not the longitudinal body is monolithically integrated into the first arm of the forceps, it may be considered that a forceps according to the present disclosure has a first arm comprising a channel extending along this arm and ending, on the side of its distal end, with a suction conduit forming the distal end.

Furthermore, the electrodes can be of various shapes and not only restricted to the shapes that are illustrated.

The invention claimed is:

1. An electrosurgical forceps, comprising:
a first arm and a second arm connected by a pivot joint for moving the arms toward and away from one another, each of the two arms having a distal end and a proximal end; and
a first electrode and a second electrode disposed at the distal ends of the first arm and the second arm, respectively;
wherein the electrosurgical forceps further comprises a channel extending in the first arm terminating at the distal end thereof in a suction conduit having a main opening and an axial opening, and the second arm carries a shutter element configured to at least partially plug the main opening of the suction conduit when the two arms are in a position moved toward one another; and
wherein the suction conduit is formed by two side walls and a base, the base of the conduit comprising a spout configured to receive the first electrode and to prevent a suction flow at a base of the first electrode.

2. The electrosurgical forceps claim 1, wherein the two side walls comprise, on internal surfaces thereof, guide elements configured to direct smoke toward the channel.

3. The electrosurgical forceps of claim 1, wherein the second electrode has a shape of a blade having a flat surface, and the shutter element comprises two flats capable of being disposed parallel to the flat surface.

4. The electrosurgical forceps of claim 1, wherein the second electrode comprises a manipulator for rotating the second electrode.

5. The electrosurgical forceps of claim 1, wherein the first arm further comprises an irrigation channel opening onto an irrigation nozzle disposed directly adjacent the first electrode.

6. The electrosurgical forceps of claim 1, wherein the channel is disposed in a longitudinal body assembled to the first arm.

7. The electrosurgical forceps of claim 6, wherein the longitudinal body is clipped to the first arm using a pair of notches disposed on a proximal part of the longitudinal body.

8. The electrosurgical forceps of claim 1, wherein the second electrode comprises a flat blade, and the shutter element comprises two flat surfaces on opposing sides of the shutter element capable of being disposed parallel to the flat blade.

9. The electrosurgical forceps of claim 8, wherein the second electrode comprises a manipulator for rotating the second electrode.

10. The electrosurgical forceps of claim 9, wherein the first arm further comprises an irrigation channel opening through irrigation nozzle disposed directly adjacent the first electrode.

11. The electrosurgical forceps of claim 10, wherein the channel is disposed in a longitudinal body assembled to the first arm.

12. The electrosurgical forceps of claim 11, wherein the longitudinal body is clipped to the first arm.

13. An electrosurgical forceps, comprising:

a first arm having a proximal end, a distal end, and a first electrode disposed at the distal end of the first arm;

a second arm having a proximal end, a distal end, and a second electrode disposed at the distal end of the second arm, the first arm and the second arm connected by a pivot joint for moving the arms toward and away from one another; and a tubular body on the first arm defining a suction channel extending therethrough between a connector proximate the proximal end of the first arm and a suction conduit proximate the distal end of the first arm, the suction conduit having a main opening and an axial opening, the suction conduit formed by two side walls and a base, the base comprising a spout to receive the first electrode; and a shutter element on the second arm, the shutter element configured to at least partially plug the main opening of the suction conduit when the first arm and the second arm are in a defined position relative to one another.

14. The electrosurgical forceps of claim 13, wherein the two side walls comprise, on internal surfaces thereof, guide elements configured to direct smoke toward the suction channel.

15. The electrosurgical forceps of claim 13, wherein the second electrode comprises a flat blade, and the shutter element comprises a generally cylindrical member having two flat surfaces on opposing sides of the generally cylindrical member, the two flat surfaces oriented parallel to the flat blade of the second electrode.

16. The electrosurgical forceps of claim 15, further comprising a manipulator for rotating the second electrode and the generally cylindrical member.

17. The electrosurgical forceps of claim 13, wherein the tubular body further defines an irrigation channel extending therethrough and opening directly adjacent the first electrode.

18. The electrosurgical forceps of claim 13, wherein the tubular body is assembled to the first arm.

\* \* \* \* \*